United States Patent
Lei et al.

(10) Patent No.: US 11,008,311 B2
(45) Date of Patent: *May 18, 2021

(54) POTASSIUM SALT OF BENZIMIDAZOLE COMPOUND AND PREPARATION METHOD THEREFOR, COMPOSITION AND APPLICATION THEREOF

(71) Applicant: WUHAN LL SCIENCE AND TECHNOLOGY DEVELOPMENT CO., LTD., Hubei (CN)

(72) Inventors: Sijun Lei, Hubei (CN); Xiang Fang, Hubei (CN); Yongkai Chen, Hubei (CN); Wei Feng, Hubei (CN); Chaodong Wang, Hubei (CN)

(73) Assignee: WUHAN LL SCIENCE AND TECHNOLOGY DEVELOPMENT CO., LTD., Hubei (CN)

( * ) Notice: Subject to any disclaimer, the term of this patent is extended or adjusted under 35 U.S.C. 154(b) by 14 days.

This patent is subject to a terminal disclaimer.

(21) Appl. No.: 16/302,030

(22) PCT Filed: May 19, 2017

(86) PCT No.: PCT/CN2017/085012
§ 371 (c)(1),
(2) Date: Nov. 15, 2018

(87) PCT Pub. No.: WO2017/198205
PCT Pub. Date: Nov. 23, 2017

(65) Prior Publication Data
US 2019/0389848 A1 Dec. 26, 2019

(30) Foreign Application Priority Data
May 20, 2016 (CN) .......................... 201610340475.4

(51) Int. Cl.
*C07D 413/10* (2006.01)
*C07D 413/14* (2006.01)
*A61P 9/12* (2006.01)

(52) U.S. Cl.
CPC .............. *C07D 413/14* (2013.01); *A61P 9/12* (2018.01); *C07D 413/10* (2013.01)

(58) Field of Classification Search
CPC ........................... C07D 413/10; C07D 413/14
See application file for complete search history.

(56) References Cited

U.S. PATENT DOCUMENTS 9,708,306 B2 * 7/2017 Ge ............................ A61P 5/50
10,611,757 B2 * 4/2020 Lei ........................ C07D 413/14

FOREIGN PATENT DOCUMENTS

| CN | 1946717 A | 4/2007 | |
|---|---|---|---|
| CN | 102351853 A | 2/2012 | |
| CN | 103709154 A | 4/2014 | |
| CN | 105753854 A * | 7/2016 | ........... C07D 413/14 |
| EP | 520423 A2 * | 12/1992 | ........... C07D 413/10 |
| WO | 2013124748 A1 | 8/2013 | |
| WO | WO-2016/145622 A1 * | 9/2016 | ........... C07D 413/10 |

OTHER PUBLICATIONS

An English machine translation of CN 103709154 A, (Ge et al.) 2014. (Year: 2014).*
Berge et al., Journal of Pharmaceutical Sciences, Jan. 1977, vol. 66, No. 1, pp. 1-19 (Year: 1977).*

* cited by examiner

*Primary Examiner* — Laura L Stockton
(74) *Attorney, Agent, or Firm* — Novick, Kim & Lee, PLLC; Allen Xue (57) ABSTRACT

The preparation method for the compound, composition and application thereof in preparing an angiotensin II receptor antagonist or application in preparing medicine for preventing and/or treating hypertension, chronic heart failure and diabetic nephropathy. After entering a human body, when releasing azilsartan, the compound releases hydroxyligustrazine or NO at the same time, thus generating a synergistic effect with azilsartan. The compound therefore has stronger and longer blood pressure lowering effect, more obvious and longer lasting heart rate lowering effect and high safety, and achieves ideal protective effect for heart and kidney functions.

12 Claims, 2 Drawing Sheets

POTASSIUM SALT OF BENZIMIDAZOLE COMPOUND AND PREPARATION METHOD THEREFOR, COMPOSITION AND APPLICATION THEREOF

FIELD OF THE INVENTION

The invention relates to the field of medicinal chemistry, in particular to a potassium salt of a benzimidazole derivative, a preparation method, a composition and an use thereof.

BACKGROUND OF THE INVENTION

Hypertension is the most common cardiovascular disease and a major risk factor for increased morbidity and mortality in congestive heart failure, stroke, coronary heart disease, renal failure, and aortic aneurysms. Antihypertensive drugs play a key role in the treatment and prevention of hypertension. With the deepening of the understanding of the pathogenesis of hypertension, many antihypertensive drugs with better curative effects, such as diuretics, β-blockers, calcium channel antagonists, angiotensin converting enzyme inhibitors (ACEI, prils), angiotensin II AT1 receptor antagonists (ABR, sartans), have been continuously discovered and successfully applied in clinical practice. After years of clinical practice, it has been confirmed that the AT1 receptor antagonists (sartans) have many advantages, especially in preventing stroke, delaying renal insufficiency of diabetes and non-diabetic nephropathy, improving left ventricular hypertrophy, and protecting the target organs due to their ability to stably lower blood pressure, to have good curative effect, long duration of action, and good patient tolerance. It does not affect the degradation of bradykinin and the synthesis of prostaglandin, so it does not cause dry cough and angioedema. Therefore, it has become the mainstream of the global antihypertensive drug market. However, the anti-hypertensive drugs of sartans have a blood pressure lowering efficiency of only about 50-60% and have a certain degree of adverse reactions. Therefore, the development of a small-dose long-acting antihypertensive drug with stronger antihypertensive effect, less adverse reactions and better protection of target organs has become a hot research direction.

The Chinese Patent Application Publication No. CN103709154A discloses for the first time a compound of the following formula II:

(II)

The above compound, as a sartan drug coupled with ligustrazine (tetramethylpyrazine) or a NO donor, is a prodrug of the angiotensin II receptor antagonist azilsartan (TAK-536). The compound could release hydroxyligustrazine or NO in vivo, thereby effectively and synergistically acting with azilsartan to enhance antihypertensive effect, produce a certain heart rate lowering effect, reduce adverse reactions, and lead an ideal protective effect on the heart and kidney of patients.

SUMMARY OF THE INVENTION

The object of the present disclosure is to provide an antihypertensive drug with more potent and longer-lasting antihypertensive effect, which has more significant and longer-lasting effect of lowering heart rate, high safety, and an ideal protective effect on heart and kidney function of the patient, and therefore can be used for preventing and/or treating hypertension, chronic heart failure, diabetic nephropathy and the like.

According to an aspect of the invention, the invention provides a compound of formula I:

(I)

wherein, R represents

-continued a=0, 1, 2, 3, 4, 5 or 6;

$R_1$ represents $C_2$-$C_8$ alkyl, $C_2$-$C_8$ alkenyl, $C_2$-$C_8$ alkynyl, $(CH_2)_nO(CH_2)_m$, phenyl, substituted phenyl, heteroaryl, or substituted heteroaryl, wherein in the group b, c=0, 1, 2, 3, 4, 5 or 6, and in the group $(CH_2)_nO(CH_2)_m$, n, m=1, 2, 3, 4, 5 or 6;

$R_2$ represents hydrogen, halogen, trifluoromethyl, $C_1$-$C_8$ alkoxy, $C_1$-$C_8$ alkyl, nitro, sulfonamido, amino or nitrile;

$R_3$ represents $C_1$-$C_8$ alkyl, $C_1$-$C_8$ alkoxy, $C_2$-$C_8$ alkenyloxy, $C_2$-$C_8$ alkynyloxy, $(C_1$-$C_6)O(C_1$-$C_6)$, aryl, substituted aryl, heteroaryl or substituted heteroaryl, wherein in the group b, c=0, 1, 2, 3, 4, 5 or 6;

$R_4$ represents aryl, substituted aryl, arylsulfonyl, heteroaryl, substituted heteroaryl, nitrile, trifluoromethyl, $C_1$-$C_8$ alkoxy, $C_1$-$C_8$ nitrate group, or $C_1$-$C_8$ alkyl;

$R_5$ represents phenyl, substituted phenyl, heteroaryl, substituted heteroaryl, nitrile, trifluoromethyl, $C_1$-$C_8$ alkoxy, $C_1$-$C_8$ nitrate, $C_1$-$C_8$ alkyl, $C_1$-$C_8$ alkenyl, $C_1$-$C_8$ alkynyl, or $(CH_2)_nO(CH_2)_m$, wherein $R_3$, $R_4$, a, m, n are as defined above;

$R_6$ and $R_7$ represent hydrogen, $C_1$-$C_8$ alkoxy or $C_1$-$C_8$ alkyl;

$R_8$ and $R_9$ represent hydrogen, $C_1$-$C_8$ alkoxy, $C_1$-$C_8$ nitrate group, or $C_1$-$C_8$ alkyl;

the substituted aryl refers to an aryl substituted with one or more selected from the group consisting of hydroxy, $C_1$-$C_6$ alkyl, $C_1$-$C_6$ alkoxy, halogen, nitro, amino, nitrile, trifluoromethyl, —CH=CHCO$_2$R$_{11}$, and each substituent may be the same or different, wherein $R_{11}$ represents hydrogen or $C_1$-$C_6$ alkyl;

the substituted heteroaryl is a heteroaryl optionally substituted with one or more selected from the group consisting of $C_1$-$C_6$ alkyl, $C_1$-$C_6$ alkoxy, halogen, and each substituent may be the same or different.

In a preferred embodiment, the compounds of the invention have the structures represented by the following formulae:

QR01005K

QR01013K

QR01008K

QR01017K

QR01009K

QR01019K

QR01011K

QR01020K

QR01023K

QR01026K

QR01030K

QR01031K

QR01032K

QR01033K

QR01034K

-continued

QR01035K

QR01036K

According to another aspect of the invention, the present disclosure also provides a method for preparing the compound of formula I, comprising the step of contacting a compound of formula II with a potassium salt reagent. The compound of formula II can be prepared by a method known in the art, for example, the method disclosed in CN103709154A, which is incorporated by reference herein in its entirety.

(II)

Wherein, the definition of R is the same as above. Taking QR01019K as an example, the preparation method comprises the step of contacting QR01019 with a potassium salt reagent, wherein the structure of OR01019 is as follows:

In the present disclosure, preferably, the compound of formula II is contacted and reacted with a potassium salt reagent in a solvent.

Those skilled in the art would understand that a wide variety of solvents can be used in the present disclosure.

Preferably, the solvent is selected from the group consisting of polar solvents, non-polar solvents, or a mixture thereof, or the solvent is selected from the group consisting of water, ether solvents, ketone solvents, alcohol solvents, ester solvents, aromatic hydrocarbon solvents, alkane solvents, nitrile solvents, or a mixture thereof. More preferably, the solvent is selected from the group consisting of methanol, ethanol, n-propanol, isopropanol, n-butanol, isobutanol, tert-butanol, methyltetrahydrofuran, tetrahydrofuran, 1,4-dioxane, ethylene glycol dimethyl ether, methyl tert-butyl ether, acetone, butyl ketone, methyl ethyl ketone, 4-methyl-2-pentanone, ethyl acetate, n-propyl acetate, isopropyl acetate, n-butyl acetate, isobutyl acetate, sec-butyl acetate, t-butyl acetate, dichloromethane, 1,2-dichloroethane, chloroform, carbon tetrachloride, nitroethane, N,N-dimethylformamide, dimethyl sulfoxide, acetonitrile, malononitrile, benzene, toluene, xylene, n-hexane, cyclohexane, pentane, n-heptane, or a mixture thereof.

It will be understood by those skilled in the art that it is not necessary to dissolve the compound of formula II completely in the solvent. Even in the absence of a solvent, the reaction may still take place after contacting the compound of formula II with the potassium salt reagent, so that any amount of solvent may be omitted or used. In a preferred embodiment, the amount of solvent used per gram of the compound of formula II is at least about 0.1 ml, further preferably from about 2 to 300 ml, more preferably from about 5 to 100 ml, and most preferably from about 10 to 50 ml.

In the present disclosure, the potassium salt reagent can be selected from the group consisting of organic acid potassium salts, inorganic acid potassium salts, or a mixture thereof. Preferably, the organic acid potassium salt is selected from the group consisting of potassium biphthalate, potassium acetate, potassium formate, potassium di-tert-butyl phosphate, dipotassium glycyrrhizinate, potassium 2-ethylhexanoate, potassium ethylxanthogenate, potassium sorbate, potassium phthalimide, potassium maleimide, potassium oxalate, potassium olefinate, potassium citrate, potassium malate, potassium gluconate, potassium lactate, potassium tartrate, potassium salicylate, potassium fumarate, potassium stearate, potassium laurate, or a mixture thereof; the inorganic acid potassium salt can be selected from the group consisting of potassium nitrate, potassium sulfate, potassium sulfite, potassium bromate, potassium hydrogencarbonate, potassium thiocyanate, dipotassium hydrogen phosphate, potassium dihydrogen phosphate, potassium hydrogen phthalate, or a mixture thereof. The potassium olefinate is selected from potassium olefinate of C3 or above, preferably potassium olefinate of C3-C26, such as potassium acrylate, potassium butenoate, potassium octadeceenoate and the like.

It will be understood by those skilled in the art that it is not necessary to dissolve the potassium salt reagent in advance. However, it may also be dissolved in the above solvent in advance. In addition, some potassium salt reagents are stored in a solvent because they are unstable or dangerous. In this case, the potassium salt reagents stored in the solvent can be used directly. In a preferred embodiment, the molar ratio of the compound of formula II to K of the potassium salt reagent is from about 1:0.3-3, more preferably about 1:0.9-2, and most preferably about 1:0.95-1.5.

In a preferred embodiment, the compound of formula II is placed in a solvent before the potassium salt reagent is added. Preferably, after the compound of formula II is placed in a solvent, the temperature may be between room temperature and the reflux temperature of the solvent; further preferably, after addition of the potassium salt reagent, the temperature may be between 0° C. and the reflux temperature of the solvent, more preferably between room temperature and the reflux temperature of the solvent. The term "room temperature" means a temperature from about 18° C. to about 30° C., preferably from about 20° C. to about 24° C., more preferably about 22° C.

It will be understood by those skilled in the art that in the present disclosure, depending on the solubility of the product in different solvents and the temperature of the reaction system after the reaction, the product may be dissolved in the solution or may be directly precipitated from the solution.

In a preferred embodiment, for the case where the product is directly precipitated from the solution, after the reaction, it is filtered and dried to give a compound of formula I. Preferably, before the filtration, it is cooled at a cooling temperature of about −50° C. to about 30° C., preferably about −10° C. to about 10° C., most preferably about 0° C. to about 5° C.

In a preferred embodiment, for the case where the product is dissolved in a solution, after the reaction, impurities are removed by filtration, the solvent in the solution is removed to give a compound of formula I or an anti-solvent is added to the solution, filtered and the residue dried to give a compound of formula I. Preferably, the solvent is removed via rotary evaporation. Preferably, before the filtration, it is cooled at a cooling temperature of about −50° C. to about 30° C., preferably about −10° C. to about 10° C., most preferably about 0° C. to about 5° C. Preferably, the anti-solvent is selected from those reagents in which the solubility of the compound is lower than that in the above solvent. For example, the anti-solvent can be selected from methyl tetrahydrofuran, tetrahydrofuran, 1,4-dioxane, ethylene glycol dimethyl ether, methyl tert-butyl ether, isopropyl ether, ethyl ether, dichloromethane, 1,2-dichloroethane, chloroform, carbon tetrachloride, nitroethane, n-hexane, cyclohexane, pentane, n-heptane, benzene, toluene, xylene, or a mixture thereof, in which the solubility is worse than in the selected solvent.

According to another aspect of the invention, the present disclosure also provides a pharmaceutical composition comprising a therapeutically effective amount of the compound of formula I. Said pharmaceutical composition can further comprise a pharmaceutically acceptable carrier according to needs. The pharmaceutical composition of the present disclosure can be formulated into powders, tablets (including various coated tablets, sustained release or controlled release tablets), troches, capsules (including soft capsules and hard capsules), granules, pills, dispersible powders, aqueous or oily suspensions, aqueous or oily solutions, emulsions, elixirs, syrups, and the like for oral administration; powders or liquid aerosols suitable for inhalation; creams, ointments, gels, aqueous or oily solutions, aqueous or oily suspensions, and the like suitable for topical use; sterile aqueous or oily injections or lyophilized powders, suppositories, and the like, suitable for parenteral administration including intravenous, subcutaneous or intramuscular injection. The pharmaceutically acceptable carriers can include, but are not limited to, excipients, lubricants, binders, disintegrants, water soluble polymers, inorganic salts, solvents, dissolution aids, suspending agents, isotonic agents, buffers, preservatives agents, antioxidants, colorants, sweeteners, sour agents, foaming agents and flavoring agents, and the like.

The pharmaceutical composition of the present disclosure may further comprise another active ingredient, such as another active ingredient for preventing and/or treating hypertension, such as calcium ion antagonist, for example, dihydropyridines, aryalkylamines, benzodiazepines, and triphenylpiperazines.

Those skilled in the art can determine suitable amounts of the compound of formula I and various pharmaceutically acceptable carriers and/or other active ingredients in the pharmaceutical compositions according to routine methods. The term "effective amount" or "therapeutically effective amount" refers to an amount of a compound according to the present disclosure sufficient to achieve the intended application, including but not limited to, the treatment of a disease as defined below. The therapeutically effective amount may vary depending on the intended application (in vitro or in vivo), or the subject and disease condition to be treated, such as the weight and age of the subject, the severity of the disease condition, and the mode of administration, and the like, which can be readily determined by those skilled in the art. The particular dosage will vary depending on the particular compound selected, the dosage regimen upon which it is administered, whether it is administered in combination with other compounds, the timing of administration, the tissue to be administered, and the physical delivery system carried.

According to another aspect of the present disclosure, the present disclosure provides the use of the compound of formula I or the pharmaceutical composition according to the present disclosure for the preparation of an angiotensin II receptor antagonist, or for the preparation of a medicament for preventing and/or treating hypertension, chronic heart failure, diabetic nephropathy.

According to another aspect of the present disclosure, the present disclosure further provides the use of the compound of formula I or the pharmaceutical composition according to the present disclosure as an angiotensin II receptor antagonist.

According to another aspect of the present disclosure, the present disclosure further provides the use of the compound of formula I or the pharmaceutical composition according to the present disclosure for preventing and/or treating hypertension, chronic heart failure, diabetic nephropathy.

The applicant also studied the salt formation reaction of the compound of formula II with other basic metal reagents. The salt including a sodium salt, magnesium salt, calcium salt, and the like. A variety of different organic and inorganic alkali metal reagents were selected and reacted with said compound. However, the obtained salts has low stability and purity, thus cannot be formulated to a medicine.

Advantages of the present disclosure include, but are not limited to:

1. As compared with the compound of formula II, the compound according to the present disclosure has more potent and longer-lasting effects of lowering blood pressure and heart rate;

2. As compared with the compound of formula II, the compound according to the present disclosure has higher solubility and bioavailability;

3. The compound according to the present disclosure would release ligustrazine or NO while releasing azilsartan in vivo, thereby effectively synergistically acting with azilsartan;

4. The compound according to the present disclosure has high safety and thus can lead an ideal protective effect on heart and kidney function of patients.

Term Explanation and Description

Unless otherwise stated, the definitions of the groups and terms recited in the specification and claims of the present application include their definitions as examples, exemplary definitions, preferred definitions, definitions in the list, and definitions of specific compounds in the examples, and the like, assembled and combined with each other arbitrarily. Such assembly and combinations of groups and compound structures are intended to fall within the scope of the present application.

Where a range of values is defined or should be understood as "integer", the numerical ranges recited in the specification and claims are to be construed as meaning the two endpoints of the range and each integer in the range. For example, $C_1$-$C_8$ should be understood to describe 1, 2, 3, 4, 5, 6, 7, and 8 carbon atoms. $C_2$-$C_8$ should be understood to describe 2, 3, 4, 5, 6, 7, and 8 carbon atoms.

The term "aryl" as used herein refers to an aromatic ring structure composed of 6 to 20 carbon atoms. For example, an aromatic ring structure comprising 6, 7 and 8 carbon atoms may be a monocyclic aromatic group such as phenyl; a ring structure comprising 8, 9, 10, 11, 12, 13 or 14 carbon atoms may be polycyclic such as naphthyl. The aromatic ring may be substituted with one or more of the above substituents at one or more ring positions.

As used herein, "heteroaryl", also referred to as "aromatic heterocycle", refers to a heteroaromatic heterocycle having at least one ring heteroatom (e.g., 1, 2, 3, 4, or 5 heteroatoms selected from O, S, or N). Heteroaryl includes single ring systems and polycyclic systems (e.g., having 2, 3 or 4 fused rings). Examples of heteroaryl groups include, but are not limited to, pyridinyl, pyrimidinyl, pyrazinyl, pyridazinyl, triazinyl, furyl, quinolinyl, isoquinolinyl, thienyl, imidazolyl, thiazolyl, indolyl, pyrrolyl, oxazolyl, benzofuranyl, benzothienyl, benzothiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, benzoxazolyl, azabenzoxazolyl, imidazothiazolyl, benzo[1,4]dioxinyl, benzo[1,3]dioxolyl, and the like. In some embodiments, a heteroaryl has 3 to 40 carbon atoms, or in other embodiments 3 to 20 carbon atoms. In some embodiments, a heteroaryl contains 3 to 14, 4 to 14, 5 to 7, or 5 to 6 ring-forming atoms. In some embodiments, a heteroaryl has 1 to 4, 1 to 3, or 1 to 2 heteroatoms. In some embodiments, a heteroaryl has 1 heteroatom.

DETAILED DESCRIPTION OF THE INVENTION

The potassium salt of the compound according to the present disclosure and preparation method and use thereof will be described in detail below in connection with exemplary embodiments. Those skilled in the art can refer to the contents herein to appropriately replace or modify the process parameters or conditions. It is to be understood that all such alternatives and modifications are intended to be included within the scope of the present application. The products and methods of the present disclosure have been described in terms of preferred embodiments, and those skilled in the art can make modifications and/or alterations and combinations of the products and/or methods described herein to implement and apply the technical solutions of the present disclosure without departing from the content, spirit and scope of the present disclosure.

Example 1

QR01019 (1.0 g) was dissolved in dichloromethane (5 ml), stirred at room temperature to form a solution, and potassium phthalimide (0.27 g) was added to the solution. The reaction was incubated for 4 hours, cooled to −50° C., filtered, and the solvent was evaporated to dryness to give a solid of amorphous QR01019K.

Melting point: 135-145° C.

MS/HRMS m/z: 717 [M+H]$^+$; 677 [M−K]$^-$.

$^1$H-NMR (400 MHz, DMSO-d$_6$) δ: 1.44 (t, 3H), 1.46 (t, 3H), 2.38 (s, 3H), 2.41 (s, 3H), 2.44 (s, 3H), 4.64 (q, 2H), 5.29 (d, 1H), 5.32 (d, 1H), 5.52 (d, 1H), 5.56 (d, 1H), 6.86 (q, 1H), 6.90 (d, 2H), 7.18 (m, 2H), 7.22 (d, 2H), 7.33 (m, 1H), 7.36 (m, 1H), 7.46 (d, 1H), 7.52 (dd, 1H), 7.75 (d, 1H).

Figure 1:
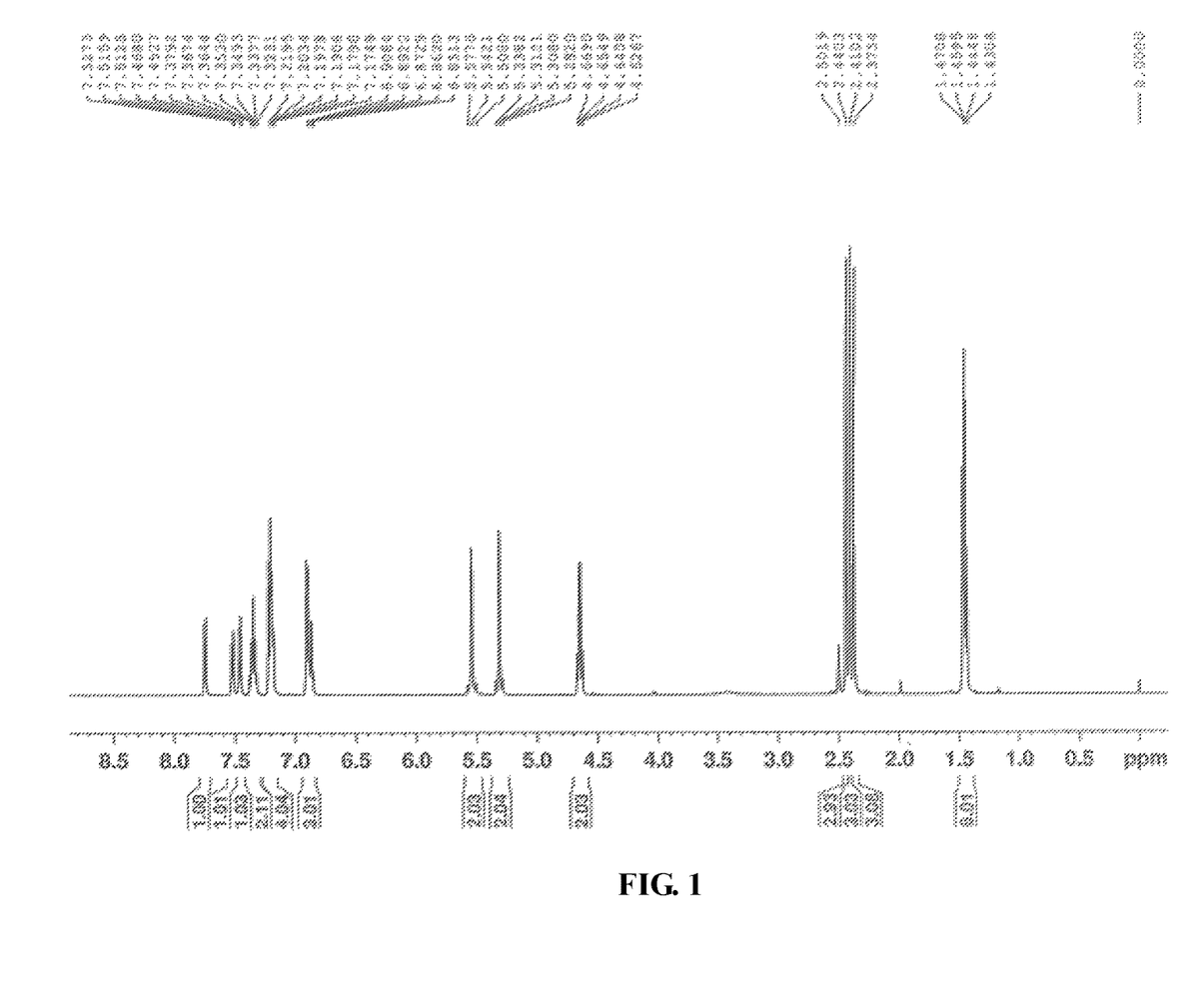
FIG. 1 is an H-NMR spectrum of QR01019K in Example 1.
Figure 2:
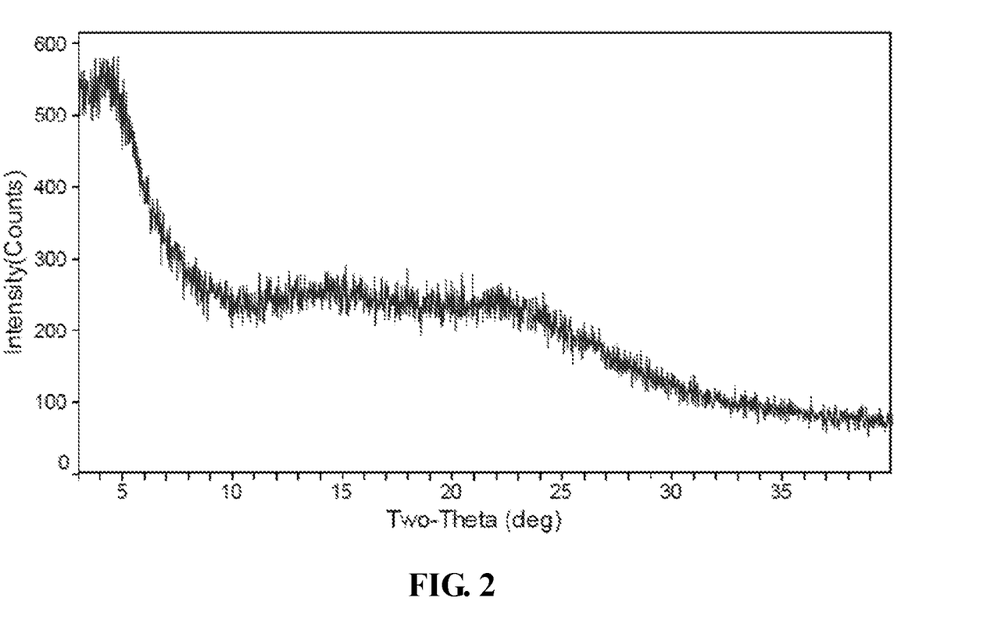
FIG. 2 is an X-ray powder diffraction spectrum of QR01019K in Example 1.

The H-NMR spectrum and the X-ray powder diffraction spectrum are shown in FIG. 1 and FIG. 2 respectively.

Example 2

The compound QR01019 (1.0 g) was dissolved in ethanol (15 ml) under reflux to form a solution. The solution was cooled to 50° C., and potassium 2-ethylhexanoate (0.30 g) in ethanol (1 ml) was slowly added dropwise to the solution. The solution was slowly cooled to 0° C., and further incubated under stirring for 5 hours, filtered, and dried under reduced pressure at 60° C. The obtained solid was amorphous QR01019K.

MS/HRMS m/z: 717 [M+H]$^+$; 677 [M−K]$^-$.

Example 3

QR01019 (1.0 g) was dissolved in dichloromethane (20 ml) under reflux to form a solution. The solution was cooled to room temperature, and potassium acetate (0.16 g) was added to the solution. The reaction was incubated for 2 hours, filtered, and the solvent was evaporated to dryness to give a solid of amorphous QR01019K.

MS/HRMS m/z: 717 [M+H]$^+$; 677 [M−K]$^-$.

Example 4

QR01019 (1.0 g) was dissolved in 1,4-dioxane (30 ml), heated to 50° C. to form a solution, and potassium phthalimide (0.27 g) was added to the solution. The reaction was incubated for 30 mins, cooled to −50° C., filtered, and the solvent was evaporated to dryness to give a solid of amorphous QR01019K.

MS/HRMS m/z: 717 [M+H]⁺; 677 [M−K]⁻.

Example 5

The compound QR01019 (1.0 g) was dissolved in acetone (20 ml) under reflux to form a solution. The solution was cooled to 40° C., and potassium 2-ethylhexanoate (0.30 g) in acetone (1 ml) was slowly added dropwise to the solution. The solution was slowly cooled to 0° C., and the mixture was further incubated under stirring for 5 hours, filtered, and dried under reduced pressure at 60° C. The obtained solid was amorphous QR01019K.

MS/HRMS m/z: 717 [M+H]⁺; 677 [M−K]⁻.

Example 6

QR01019 (1.0 g) was dissolved in dichloromethane (5 ml), stirred at room temperature to form a solution, and potassium maleimide (0.20 g) was added to the solution. The reaction was incubated for 4 hours, cooled to −50° C., filtered, and the solvent was evaporated to dryness to give a solid of amorphous QR01019K.

MS/HRMS m/z: 717 [M+H]⁺; 677 [M−K]⁻.

Example 7

QR01019 (1.0 g) was dissolved in N,N-dimethylformamide (5 ml), stirred at room temperature to form a solution, and potassium nitrate (0.15 g) was added to the solution. The temperature was raised to 30° C., and the reaction was incubated for 4 hours, cooled to room temperature, filtered. 100 ml of n-hexane was added to the filtrate, filtered and the obtained solid was amorphous QR01019K.

MS/HRMS m/z: 717 [M+H]⁺; 677 [M−K]⁻.

Example 8

QR01019 (1.0 g) was dissolved in dimethyl sulfoxide (5 ml), stirred at room temperature to form a solution, and potassium thiocyanate (0.14 g) was added to the solution. The temperature was raised to 40° C., and the reaction was incubated for 4 hours, cooled to room temperature and filtered. 100 ml of methyl tert-butyl ether was added to the filtrate, filtered and the obtained solid was amorphous QR01019K.

MS/HRMS m/z: 717 [M+H]⁺; 677 [M−K]⁻.

Example 9

QR01019 (1.0 g) was dissolved in tetrahydrofuran (5 ml), stirred at room temperature to form a solution, and dipotassium hydrogen phosphate (0.20 g) was added to the solution. The reaction was incubated for 4 hours, cooled to −50° C., filtered, and the solvent was evaporated to dryness to give a solid of amorphous QR01019K.

MS/HRMS m/z: 717 [M+H]⁺; 677 [M−K]⁻.

Example 10

QR01019 (1.0 g) was dissolved in 1,4-dioxane (5 ml), heated to 50° C. under stirring to form a solution, and potassium dihydrogen phosphate (0.20 g) was added to the solution. The reaction was incubated for 4 hours, cooled to room temperature, filtered, and the solvent was evaporated to dryness to give a solid of amorphous QR01019K.

MS/HRMS m/z: 717 [M+H]⁺; 677 [M−K]⁻.

Example 11: Preparation of QR01019 Sodium Salt

QR01019 (0.5 g) was dissolved in toluene (2.5 ml), heated to 80° C. to form a solution, cooled to room temperature, and 60% sodium hydride (0.029 g) was added to the solution. The reaction was stirred for 4 hours, and n-hexane (25 ml) was added to the reaction mixture to precipitate a solid, which was filtered and dried to give a solid of QR01019 sodium salt.

MS: 701 [M+H]⁺; 677 [M−Na]⁻.

¹H-NMR (400 MHz, DMSO-$d_6$) δ: 1.40 (d, 3H), 1.41 (t, 3H), 2.35 (s, 3H), 2.39 (s, 3H), 2.40 (s, 3H), 4.61 (q, 2H), 5.27 (q, 2H), 5.49 (q, 2H), 6.80 (q, 1H), 6.83 (d, 2H), 7.15 (m, 4H), 7.32 (td, 2H), 7.43 (m, 2H), 7.72 (dd, 1H).

Example 12: Antihypertensive Efficacy Test of QR01019K in Spontaneously Hypertensive Rats 12-week-old spontaneously hypertensive rats (hereinafter referred to as SHR, purchased from Beijing Vital River Laboratory Animal Technology Co., Ltd.) were anesthetized with 2.5% sodium pentobarbital for intraperitoneal injection. The blood pressure sensing catheter of a blood pressure implant was inserted into the abdominal aorta, the implant was fixed to the abdominal wall, and the postoperative daily care was performed after suturing. Animals with systolic blood pressure exceeding 160 mmHg were selected into a total of 3 groups with 8 animals in each group. The control group was given 0.5% CMC-Na (sodium carboxymethylcellulose); in the QR01019 group and the QR01019K group, the compounds were dissolved in 0.5% CMC-Na, and the doses were all administered at an effective dose of 1 mg/kg of azilsartan with an administration volume of 4 mL/kg by intragastric administration. The systolic blood pressure and heart rate of the animals before the administration were used as reference values, and the changes of systolic blood pressure and heart rate of SHR at each time point before and after administration were compared, in which the systolic blood pressure and heart rate of SHR were measured three times at each time point and then averaged. The results are shown in Tables 1 and 2 below.

TABLE 1

Changes in systolic blood pressure at each time point before and after the oral administration of QR01019 and QR01019K (mean value (mmHg) ± standard error)

| Groups | Before administration | 1 hour after administration | 3 hours after administration | 5 hours after administration |
|---|---|---|---|---|
| Control group | 0.0 ± 0.0 | 5.4 ± 7.1 | −3.5 ± 4.6 | 4.5 ± 4.0 |
| QR01019 group | 0.0 ± 0.0 | −4.9 ± 4.8 | −22.0 ± 3.6* | −30.5 ± 3.5* |
| QR01019K group | 0.0 ± 0.0 | −7.0 ± 3.4 | −34.3 ± 1.9* | −46.5 ± 2.5* |

| Groups | 7 hours after administration | 10 hours after administration | 24 hours after administration |
|---|---|---|---|
| Control group | 4.1 ± 3.2 | −2.9 ± 2.3 | −2.7 ± 6.4 |
| QR01019 group | −38.8 ± 2.3* | −33.0 ± 1.7* | −10.2 ± 2.1 |
| QR01019K group | −49.4 ± 4.1* | −45.3 ± 3.3* | −25.9 ± 3.4* |

*P < 0.01 (relative to the control group).

It can be seen from the results in Table 1 that 3 hours after the administration, as compared with the control group, all administration groups showed significantly decreased systolic blood pressures. Furthermore, all administration groups achieved drug efficacy peak times of 5 to 7 hours after the administration, and the QR01019K group had a more potent and longer-lasting antihypertensive effect than QR01019.

TABLE 2

Change in heart rate at each time point before and after the oral administration of QR01019 and QR01019K (mean value (times/minute) ± standard error)

| Groups | Before administration | 1 hour after administration | 3 hours after administration | 5 hours after aadministration |
|---|---|---|---|---|
| Control group | 0.0 ± 0.0 | 0.14 ± 2.9 | 6.4 ± 2.8 | −0.3 ± 2.7 |
| QR01019 group | 0.0 ± 0.0 | −3.4 ± 2.6 | −2.33 ± 2.6* | −6.5 ± 2.8* |
| QR01019K group | 0.0 ± 0.0 | −3.6 ± 2.4 | −5.0 ± 2.5* | −10.1 ± 3.0* |

| Groups | 7 hours after administration | 10 hours after administration | 24 hours after administration |
|---|---|---|---|
| Control group | −0.1 ± 2.9 | −2.5 ± 2.5 | 4.3 ± 2.8 |
| QR01019 group | −6.2 ± 3.0* | −12.3 ± 2.8* | −6.7 ± 2.6* |
| QR01019K group | −17.5 ± 3.0* | −25.4 ± 2.4* | −28.6 ± 8* |

*$P < 0.05$ (relative to one-way variance comparison of the control group).

As can be seen from Table 2, the QR01019K group had a more potent and longer-lasting effect of reducing heart rate than QR01019.

The efficacy test of the following compounds (potassium salts) was also performed according to the above method, showing that as similar to QR01019K, these compounds had more potent and longer-lasting effects of lowering blood pressure and heart rate effects than their corresponding unsalted compounds.

QR01005K

QR01008K

QR01009K

QR01011K

QR01013K

-continued

QR01017K

QR01020K

QR01023K

QR01026K

-continued

QR01030K

QR01031K

QR01032K

-continued

QR01033K

QR01034K

QR01035K

QR01036K

Example 13: Pharmacokinetic Study

12 SD rats, SPF grade, weighing 180-220 g (purchased from Beijing Vital River Laboratory Animal Technology Co., Ltd.) were taken with half male and half female. They were randomly divided into 2 groups with 6 in each group, 3 males and 3 females. QR010109 and QR01019K were dissolved in 0.5% CMC-Na with a drug concentration of 0.1 mg/mL based on azilsartan, and administered intragastrically in an administration volume of 10 ml/kg and a dose of 1.0 mg/kg based on azilsartan. Blood was collected from the jugular vein at different time points after administration (before administration and 0.25, 0.5, 1, 2, 3, 4, 6, 8, 10, and 24 hours after administration, respectively), blood samples were collected, and the concentrations of plasma azisartan were measured. The various pharmacokinetic parameters are shown in Table 3 below.

TABLE 3

Main pharmacokinetic parameters of single intravenous administration of each compound in rats

| Compounds | $C_{max}$ (ng/mL) | $T_{max}$ (hr) | $AUC_{0-24}$ (ng/mL*hr) | $T_{1/2}$ (hr) |
|---|---|---|---|---|
| QR01019  | 1254 ± 390 | 0.58 ± 0.20 | 6386 ± 1220  | 6.16 ± 1.01 |
| QR01019K | 3735 ± 803 | 0.5 ± 0.0   | 18573 ± 2919 | 7.51 ± 1.60 |

$C_{max}$: Blood drug peak concentration,
$T_{max}$: Blood pressure peak time,
$AUC_{last}$: Area under the time curve,
$T_{1/2}$: Half life As can be seen from the results in Table 3, the bioavailability of QR01019 is about ⅓ of that of QR01019K.

Example 14: Stability Test of the Compounds

The applicants investigated the stability of the compounds by taking 200 mg of each of QR01019K and QR01019 sodium salt compounds which were subjected to the following test:

an inner self-sealing PVC bag containing the test compound was vacuumed and an aluminum foil as an interlayer was used to wrap the inner PVC bag and then was vacuumed. Further, another aluminum foil, as an outer layer wrapping the interlayer together with a desiccant, was vacuumed and then charged with nitrogen gas; examination conditions: 25° C., 60% humidity. The index of inspection was the total impurity content. Samples were taken at different time points, and at each time point three samples were taken and tested to give an average value. The sampling time points were day 0, day 15, and day 30. The compound prepared in Example 11 could not be improved in purity to meet the drug purity standard. The test results are shown in Table 4 below.

TABLE 4

Stability test (% total impurity content)

| Investigated compound | Sampled time (day) | | |
|---|---|---|---|
| | 0 | 15 | 30 |
| QR01019K | 1.52 | 5.95 | 13.28 |
| QR01019 sodium salt | 20.76 | 29.47 | 43.25 |

Example 15: Determination of Equilibrium Solubility of QR01019 Potassium Salt 20 mg of each of QR01019 and QR01019K was weighed respectively, put into 10 mL of a dissolution medium, and shaken at 37±2° C., 250 r/min for 24 h, and the equilibrium solubility was measured. The results are shown in Table 5 below.

TABLE 5

| Dissolving medium | equilibrium solubility for 24 h (μg/ml) | |
| --- | --- | --- |
|  | QR01019, based on azilsartan | QR01019K, based on azilsartan |
| pH 1.0 (hydrochloric acid solution) | 2.01 | 18.70 |
| pH 4.5 (acetate buffer) | 0.06 | 2.30 |
| pH 6.8 (phosphate buffer) | 1.60 | 25.90 |
| pH 7.8 (phosphate buffer) | 13.60 | 400.50 |
| Pure water | 0.74 | 542.00 |

It can be seen from Table 5 that the addition concentrations of QR01019K in both acidic and neutral media are much higher than QR01019.

The invention claimed is:

1. Compound of formula I:

QR01019K (I)

2. A method for preparing the compound according to claim 1, comprising:
    reacting a compound of formula II with a potassium salt reagent in a solvent to form the compound of formula I, (II)

3. The preparation method according to claim 2, wherein the solvent is selected from water, ether solvents, ketone solvents, alcohol solvents, ester solvents, aromatic hydrocarbon solvents, alkane solvents, nitrile solvents, and a mixture thereof.

4. The preparation method according to claim 2, wherein the potassium salt reagent is one or more organic acid potassium salts, one or more inorganic acid potassium salts, or a mixture thereof;
    wherein the organic acid potassium salt is selected from potassium biphthalate, potassium acetate, potassium formate, potassium di-tert-butyl phosphate, dipotassium glycyrrhizinate, potassium 2-ethylhexanoate, potassium ethylxanthogenate, potassium sorbate, potassium phthalimide, potassium maleimide, potassium oxalate, potassium olefinate, potassium citrate, potassium malate, potassium gluconate, potassium lactate, potassium tartrate, potassium salicylate, potassium fumarate, potassium stearate, and potassium laurate, and
    wherein the inorganic acid potassium salt is selected from potassium nitrate, potassium sulfate, potassium sulfite, potassium bromate, potassium hydrogencarbonate, potassium thiocyanate, dipotassium hydrogen phosphate, potassium dihydrogen phosphate, and potassium hydrogen phthalate.

5. The preparation method according to claim 4, further comprising adding the compound of formula II into the solvent to form a first solution; adding the potassium salt into the first solution to form a reaction mixture; and
    maintaining a temperature of the reaction mixture between room temperature and a reflux temperature of the solvent.

6. The preparation method according to claim 5, further comprising: cooling the temperature of the reaction mixture to between about −10° C. to about 10° C.; obtaining the compound of formula I after filtration and drying.

7. The preparation method according to claim 5, further comprising adding an anti-solvent to the reaction mixture; filtering and drying a solid to obtain the compound of formula I;
    wherein the anti-solvent is selected from methyl tetrahydrofuran, tetrahydrofuran, 1,4-dioxane, ethylene glycol dimethyl ether, methyl tert-butyl ether, isopropyl ether, ethyl ether, dichloromethane, 1,2-dichloroethane, chloroform, carbon tetrachloride, nitroethane, n-hexane, cyclohexane, pentane, n-heptane, benzene, toluene, xylene, and a mixture thereof.

8. A pharmaceutical composition, comprising a therapeutically effective amount of the compound according to claim 1 and a pharmaceutically acceptable carrier.

9. A method for treating hypertension, comprising administering an effective amount of the compound according to claim 1.

10. The preparation method of claim 2, wherein the solvent is selected from methanol, ethanol, n-propanol, isopropanol, n-butanol, isobutanol, tert-butanol, methyltetrahydrofuran, tetrahydrofuran, 1,4-dioxane, ethylene glycol dimethyl ether, methyl tert-butyl ether, acetone, butyl ketone, methyl ethyl ketone, 4-methyl-2-pentanone, ethyl acetate, n-propyl acetate, isopropyl acetate, n-butyl acetate, isobutyl acetate, sec-butyl acetate, t-butyl acetate, dichloromethane, 1,2-dichloroethane, chloroform, carbon tetrachloride, nitroethane, N,N-dimethylformamide, dimethyl sulfoxide, acetonitrile, malononitrile, benzene, toluene, xylene, n-hexane, cyclohexane, pentane, n-heptane, and a mixture thereof.

11. The preparation method of claim 2, wherein a ratio between a volume of solvent to per gram of the compound of formula II is 5 to 100 ml.

12. The preparation method of claim 4, wherein a molar ratio between the compound of formula II to K of the potassium salt reagent is about 1:0.3-3.

* * * * *